United States Patent
Shirahata

(10) Patent No.: US 9,135,702 B2
(45) Date of Patent: Sep. 15, 2015

(54) IMAGE DISPLAY DEVICE FOR MEDICAL APPLICATIONS, IMAGE DISPLAY METHOD FOR MEDICAL APPLICATIONS

(75) Inventor: Takashi Shirahata, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 81 days.

(21) Appl. No.: 14/112,103

(22) PCT Filed: Feb. 22, 2012

(86) PCT No.: PCT/JP2012/054271
§ 371 (c)(1),
(2), (4) Date: Oct. 16, 2013

(87) PCT Pub. No.: WO2012/144266
PCT Pub. Date: Oct. 26, 2012

(65) Prior Publication Data
US 2014/0037167 A1    Feb. 6, 2014

(30) Foreign Application Priority Data

Apr. 20, 2011   (JP) ................. 2011-093569

(51) Int. Cl.
| G06T 7/00  | (2006.01) |
| G06K 9/00  | (2006.01) |
| A61B 5/00  | (2006.01) |
| A61B 5/055 | (2006.01) |
| A61B 6/03  | (2006.01) |
| A61B 6/00  | (2006.01) |

(52) U.S. Cl.
CPC .......... *G06T 7/0012* (2013.01); *A61B 5/0033* (2013.01); *A61B 5/055* (2013.01); *A61B 5/742* (2013.01); *A61B 6/03* (2013.01); *A61B 6/466* (2013.01)

(58) Field of Classification Search
None
See application file for complete search history.

(56) References Cited

U.S. PATENT DOCUMENTS

| 2006/0023924 A1 | 2/2006 | Asbeck et al. |
| 2006/0193510 A1 | 8/2006 | Matsumoto |
| 2009/0016483 A1* | 1/2009 | Kawasaki et al. ............ 378/4 |
| 2010/0316272 A1* | 12/2010 | Kadir et al. .............. 382/128 |

FOREIGN PATENT DOCUMENTS

| JP | 2006-34983 | 2/2006 |
| JP | 2006-238938 | 9/2006 |
| JP | 4200546 | 10/2008 |
| JP | 2009-34494 | 2/2009 |
| JP | 2010-306 | 1/2010 |
| JP | 2010-131315 | 6/2010 |

OTHER PUBLICATIONS

International Search Report in PCT/JP2012/054271.
International Preliminary Report dated Oct. 3 2013 in International application No. PCT/JP2012/054271.

* cited by examiner

*Primary Examiner* — Siamak Harandi
(74) *Attorney, Agent, or Firm* — Cooper & Dunham LLP

(57) ABSTRACT

An image display device such as a medical image display device is provided for supporting that information necessary for diagnosis is sufficiently displayed and the diagnosis without any error is conducted in a short period of time. The medical image display device 1 performs a region of interest setting process for setting a region of an observation site in volume data and a lesion candidate region relating to the observation site, a display image generating process for generating a display image that allows a size of the lesion candidate region to be distinguishable, being adjacent to the observation site on a projection line of interest, when a pixel having a reference pixel value on the projection line of interest corresponds to a pixel of the region of the observation site, and an image displaying process for displaying the display image being generated.

7 Claims, 11 Drawing Sheets

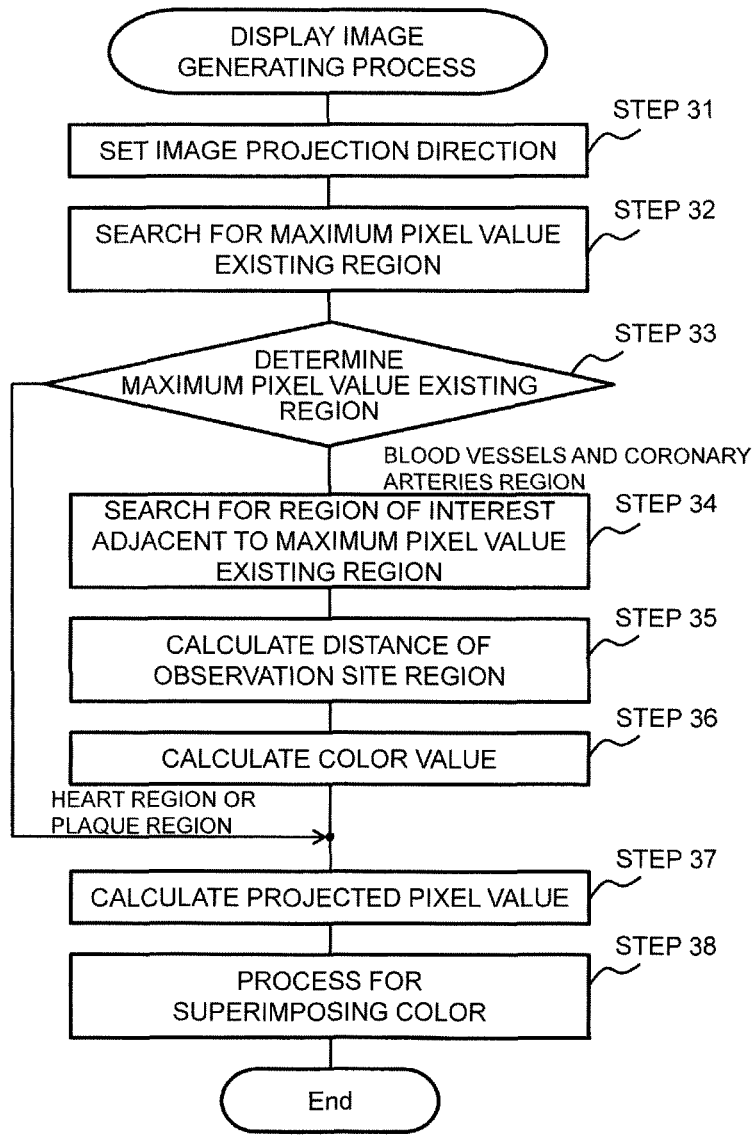

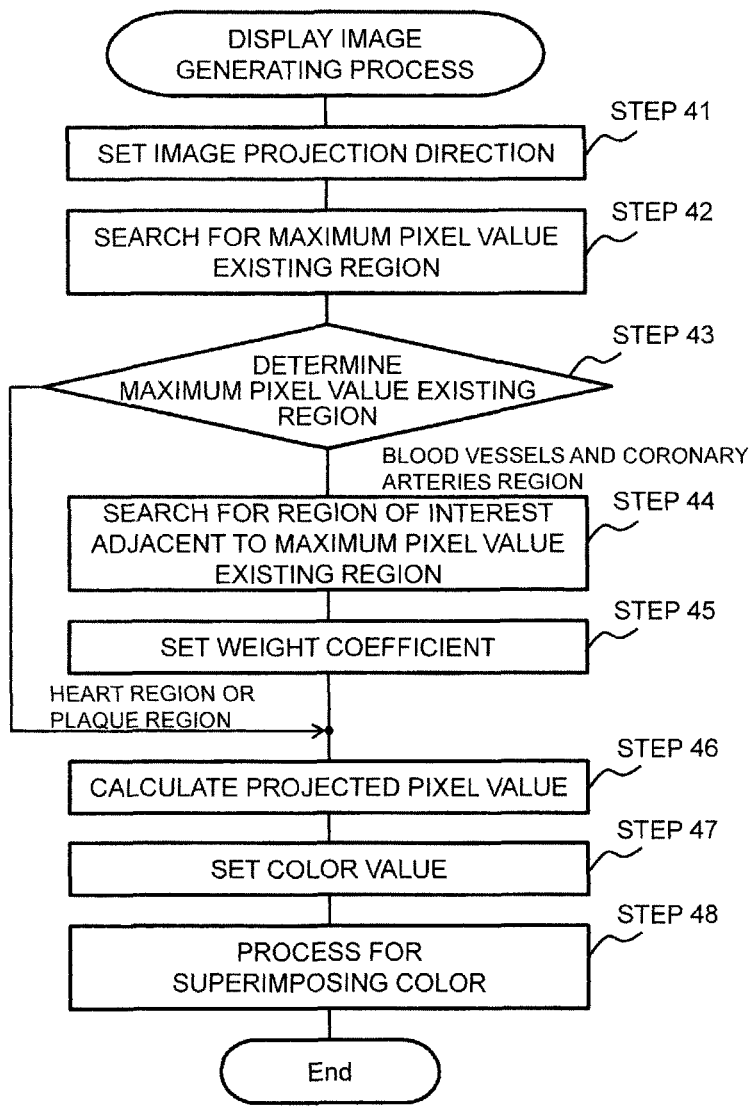

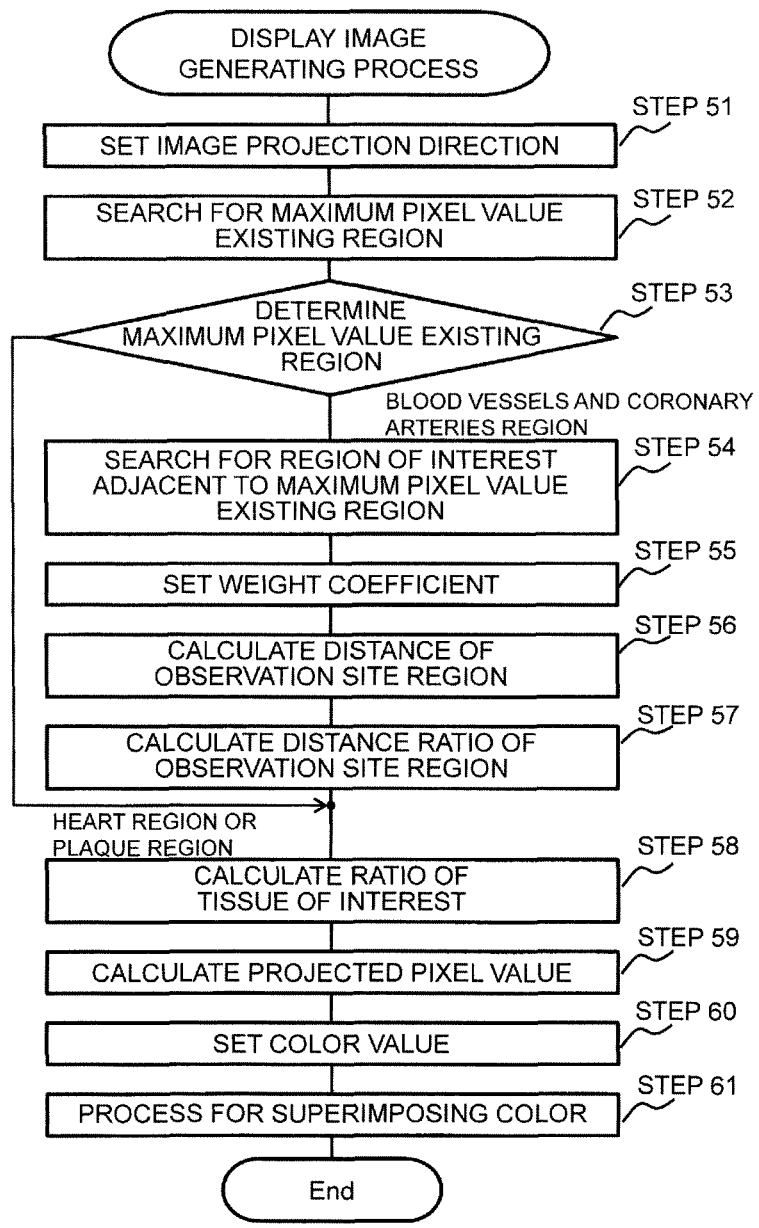

IMAGE DISPLAY DEVICE FOR MEDICAL APPLICATIONS, IMAGE DISPLAY METHOD FOR MEDICAL APPLICATIONS

TECHNICAL FIELD

The present invention relates to an image display device such as a medical image display device for displaying a medical image that is obtained from a medical image diagnostic device, including an X-ray CT scanner, an MRI apparatus, an ultrasonic apparatus, and a nuclear medicine diagnostic apparatus. More specifically, the present invention relates to an image display device such as a medical image display device for extracting a region of a hollow organ and a region on the periphery thereof, and displaying information such as positional information, shape information, and image density information of the hollow organ, and further displaying composition information, and the like, of the region on the periphery of the hollow organ.

BACKGROUND ART

Upon performing a diagnostic on a blood vessel, it is necessary to observe not only whether or not there exists any change in a vascular diameter and a degree thereof due to plaque and the like, and a difference how the vascular diameter changes, concentrically or eccentrically, but also whether or not any abnormality exists, and positional information and composition information thereof, including information such as compensatory enlargement without changing the vascular diameter, a property of the plaque (a ratio of lipid), and a place where such abnormality exists. In recent years, by the improvement of spatial resolution and temporal resolution of the medial image diagnostic device, it is becoming possible to acquire information, such as whether or not any abnormality exists, the positional information and the composition information thereof, from a medical image.

In general, it is difficult to simultaneously provide information such as whether or not an abnormality exists, the positional information, and the composition information, using only one image. Conventionally, observations are performed by combining more than one image, such as a tomographic image orthogonal to a blood vessel and an image cut by a curved surface along a traveling direction of the blood vessel as described in the patent document 1, for instance. Furthermore, the patent document 2 describes that a display is created by superimposing information relating to depth, on an X-ray perspective projection image that is displayed as a guide image when PCI (Percutaneous Coronary Intervention) treatment is applied.

PRIOR ART DOCUMENT

Patent Document

Patent Document 1
   Japanese Patent No. 4200546
Patent Document 2
   Japanese Unexamined Patent Application Publication No. 2009-034494

DISCLOSURE OF THE INVENTION

Problem to be Solved by the Invention

In a tomographic image being orthogonal to a blood vessel, however, it is unclear where an abnormality exists, and further, it is not possible to observe in what range the abnormality exists along the traveling direction of the blood vessel. On the other hand, in the image obtained by a curved cut surface along the traveling direction of the blood vessel, as described in the patent document 1, it is possible to know in what range the abnormality exists with respect to the traveling direction of the blood vessel. However, if there is an eccentric abnormality, the abnormal portion may not be displayed on the image, depending on the direction of the curved cut surface, and this may cause an error, or it takes immense amount of time for diagnosis because it is necessary to make observation with changing the curved surface.

By a simple maximum intensity projection or volume rendering method, it is not possible to depict plaque regions being unevenly distributed in the direction along the projection line. On the other hand, the technique as described in the patent document 2 allows to know whether a lesion part in a blood vessel exists, in front of or behind a three-dimensional vessel core line, with respect to the projection direction. However, as described above, in vascular diagnosis, it is necessary to observe not only whether or not there exists any change in a vascular diameter and a degree thereof, due to plaque and the like, and a difference how the vascular diameter changes, concentrically or eccentrically, but also whether or not any abnormality exists, and the positional information and the composition information thereof, including information such as compensatory enlargement without changing the vascular diameter, a property of the plaque (a ratio of lipid), and a place where such abnormality exists. Therefore, only the information relating to the depth as described in the patent document 2 is not sufficient for displaying information that is required for the vascular diagnosis.

The present invention has been made in view of the aforementioned problem, and an object of the present invention is to provide a medial image displaying technique for sufficiently displaying information necessary for diagnosis, and supporting that the diagnosis without error is conducted in a short period of time.

Means to Solve the Problem

In order to achieve the aforementioned object, a first aspect of the present invention is directed to a medical image display device that is provided with a region of interest setter for setting a first region of interest being a region of an observation site in volume data, and a second region of interest being a lesion candidate region relating to the observation site, a display image generator for generating a display image that allows a size of an adjacent second region of interest to be distinguishable, being the second region of interest adjacent to the first region of interest on a projection line of interest, when a pixel having a reference pixel value on the projection line of interest corresponds to a pixel of the first region of interest, and a display unit for displaying the display image.

A second aspect of the present invention is directed to a medical image display method that is provided with a region of interest setting step of setting a first region of interest being a region of an observation site in volume data, and a second region of interest being a lesion candidate region relating to the observation site, a display image generation step of generating a display image that allows a size of an adjacent second region of interest to be distinguishable, being the second region of interest adjacent to the first region of interest on a projection line of interest, when a pixel having a reference pixel value on the projection line of interest corresponds to a pixel of the first region of interest, and a displaying step of displaying the display image.

Effect of the Invention

According to the present invention, it is possible to provide a medical image displaying technique for sufficiently displaying information necessary for diagnosis, and supporting that the diagnosis without error is conducted in a short period of time.

BRIEF DESCRIPTION OF DRAWINGS

FIG. 8 is a flowchart illustrating the display image generating process according to the second embodiment;
FIG. 10 is a flowchart illustrating the display image generating process according to the third embodiment;
FIG. 11 is a flowchart illustrating the display image generating process according to the fourth embodiment.

BEST MODE FOR CARRYING OUT THE INVENTION

With reference to the accompanying drawings, preferred embodiments of the present invention will be explained in detail. Hereinafter, components having the same function are labeled the same, and tedious explanations will not be made. Firstly, with reference to FIG. 1 and FIG. 2, the hardware configuration and processing of the medical image display device 1 commonly described in all the preferred embodiments will be schematically explained.

Figure 1:
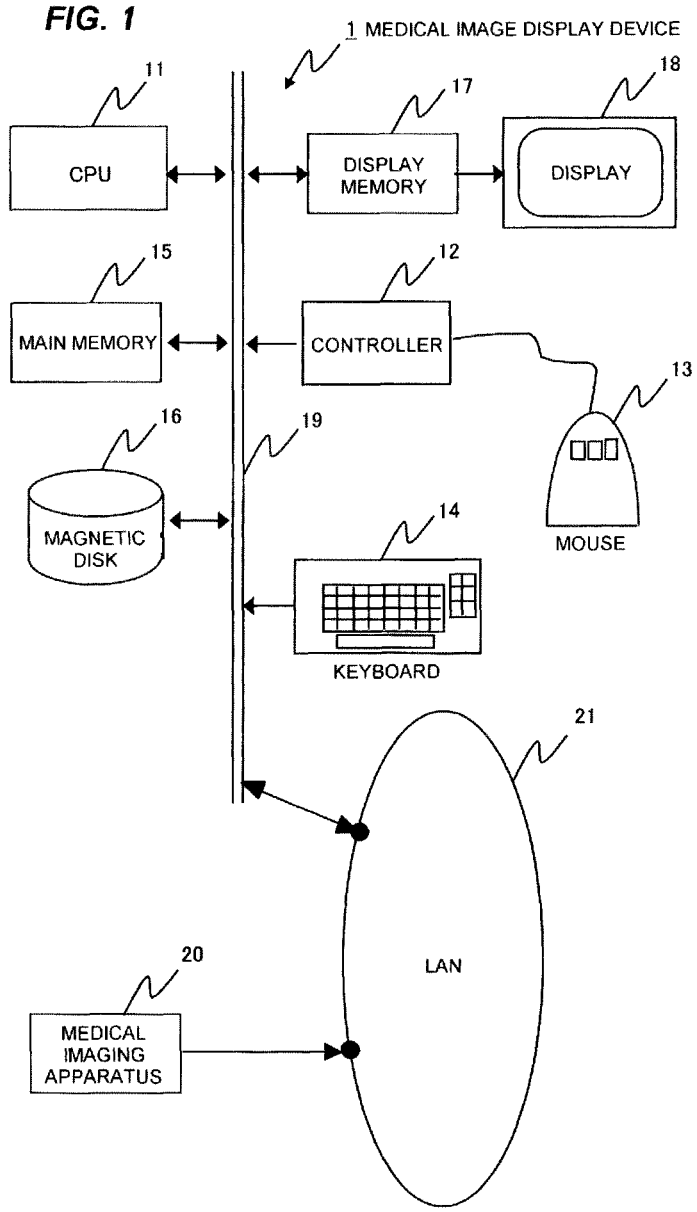
FIG. 1 is a hardware configuration diagram illustrating a medical image display device.

As illustrated in FIG. 1, in the medical image display device 1, a controller 12, a keyboard 14, a main memory 15, a magnetic disk 16, and a display memory 17, are each connected to a CPU 11 via a data transfer bus 19, in such a manner as allowing transmission and reception of signals. The CPU 11 is also connected to a medical imaging apparatus 20 via the data transfer bus 19 and a local area network (LAN) 21, in such a manner as allowing transmission and reception of signals. The controller 12 is connected to a mouse 13 in such a manner as allowing transmission and reception of signals. The display memory 17 is connected to a display 18 in such a manner as allowing transmission and reception of signals. Here, the phrase "in such a manner as allowing transmission and reception of signals" indicates the state where a signal is transmittable and receivable mutually or from one side to the other, electrically or optically, via any means, in a wired manner or a wireless manner.

The CPU 11 executes computer programs and controls each of those elements being connected. The computer programs may be commands directed to the CPU 11, combining the following, for example; extraction of a region of the hollow organ included in the medical image data, extraction of a region corresponding to the inside of the hollow organ and a region of lesion candidate (such as plaque) on the periphery thereof, and extraction of regions of other organs surrounding the hollow organ region, in order to obtain an execution result such as generation of display image based on the information of thus extracted regions.

The controller 12 transfers various data to the CPU 11 via the data transfer bus 19, the various data including positional displacement amount data obtained by a sensor provided in the mouse 13, and input data, and the like, from a button switch provided on the mouse 13. The mouse 13 supports data inputting by an operator. When the operator moves the cursor of the mouse 13 onto a switch or the like, created by software, such as an image and a radio switch displayed on the display 18, and clicks the position being a destination, predetermined inputted data is transferred to the CPU 11. The keyboard 14 is an input device that is appropriate for character inputting, such as ID information for specifying a medical image to be read out from the magnetic disk 16, and for a medical image diagnostic report to be shown on the display 18.

The main memory 15 is used as a work area of the CPU 11, for the cases such as loading various computer programs from the magnetic disk 16 and storing medical image data and a result of an operation still in progress, when the CPU 11 executes the various computer programs. The magnetic disk 16 stores various computer programs. In addition, the magnetic disk 16 receives via the LAN 21 and the data transfer bus 19 a tomographic image of a test subject being imaged by the medical imaging apparatus 20, and stores the tomographic image. The magnetic disk 16 is one example of an external storage device in a computer system. The external storage device may include any storage medium, such as a flexible disk, an optical (magnetic) disk, a ZIP memory, and a USB memory.

The display memory 17 temporarily stores the data to be displayed on the screen, out of the results of operations by the CPU 11, before transferring signals to the display 18. The display 18 displays the medical image and accompanying various information, transferred as signals from the display memory 17.

The data transfer bus 19 performs data transfer between each of the elements being connected to the data transfer bus 19. The medical imaging apparatus 20 may be a device for obtaining a tomographic image of the test subject, such as an X-ray CT scanner, an MRI apparatus, an ultrasound apparatus, a scintillation camera apparatus, PET device, and SPECT apparatus. The LAN 21 establishes connection between the medical imaging apparatus 20 and the medical image display device 1 in such a manner as allowing transmission and reception of signals. It is to be noted that instead of the LAN 21, a public line such as the Internet may be applicable.

In the aforementioned explanation, the display 18 serving as the display device, and the mouse 13 and the keyboard 14 serving as the input device, are separated. However, the display device and the input device may be integrated as a touch-panel type display, or the like.

Next, a brief overview of the processing in the medical image display device 1 will be explained. Here in the explanation, the heart and coronary arteries imaged by an X-ray CT scanner are taken as an example of the observation target. It is to be noted that the medical imaging apparatus 20 is not limited to the X-ray CT scanner. An organ targeted for the observation is not limited to the heart and coronary arteries. The targeted organ may be a blood vessel other than the coronary arteries, or other organs such as a bronchial tube.

Figure 2:
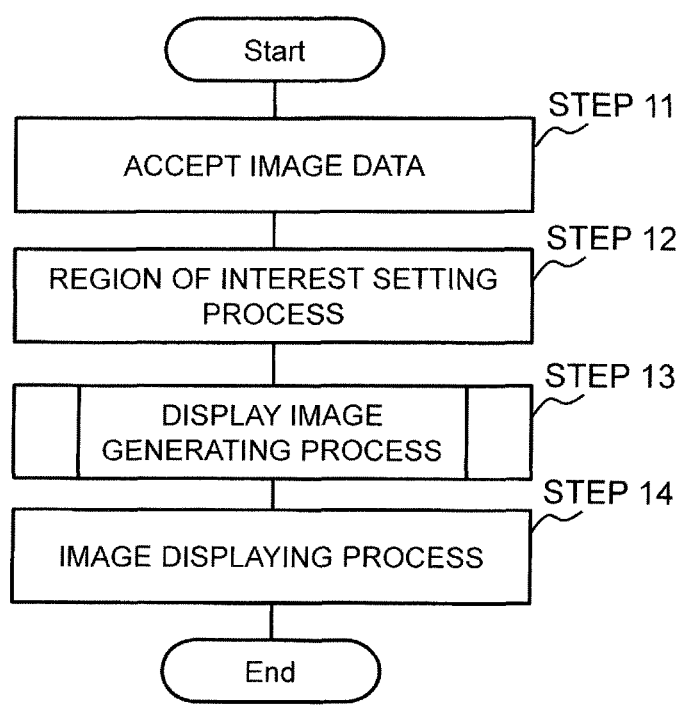
FIG. 2 is a flowchart schematically illustrating a process in the medical image display device.

As shown in FIG. 2, the operator manipulates the input device such as the mouse 13 and the keyboard 14, and selects a volume data item used as an observation target, from a group of volume data items being imaged by the medical imaging apparatus 20. Then, the CPU 11 of the medical image display device 1 accepts the volume data item being selected (step 11).

Next, the CPU 11 performs the process for setting a region of interest (step 12). The CPU 11 extracts from the volume data item being accepted, a region being the observation target organ according to the present embodiment, a heart region, a blood vessels and a coronary arteries region, or a plaque region on the periphery of the blood vessels and coronary arteries region. Then, the CPU 11 sets thus extracted region as the region of interest. On this occasion, it is configured in such a manner that each region of interest is identifiable as which of the following regions; the heart region, the blood vessels and coronary arteries region, or the plaque region on the periphery of the blood vessels and coronary arteries. The CPU 11 extracts the region by a threshold processing by using pixel value information such as a CT value, for instance. By way of example, in the case of CT imaging by the use of a contrast agent, there is a large difference between the CT value of the blood vessels and coronary arteries into which the contrast agent is injected, and the CT value of the plaque existing on the periphery of the blood vessels and coronary arteries. Therefore, this allows the CPU 11 to easily discriminate between the region of the blood vessels and coronary arteries, and the plaque region on the periphery of the blood vessels and coronary arteries. It is to be noted that in the case of an MRI apparatus, since the pixel value varies depending on an imaging method, the threshold value in the threshold processing is changed appropriately for the imaging method being employed.

Alternatively, the operator may designate positional information of the region of interest, by using the input device such as the mouse 13, on the image of the observation target displayed on the display 18, and the CPU 11 may extract the region based on the positional information being designated.

In the aforementioned explanation, the CPU 11 sets as the region of interest, any of the following three regions, the heart region, the blood vessels and coronary arteries region, and the plaque region on the periphery of the blood vessels and coronary arteries region, but the region of interest to be set is not limited to this example. It is considered to be sufficient that the CPU 11 sets at least a region of the observation site (e.g., the blood vessels and coronary arteries region) in the volume data, and a region of a lesion candidate relating to the observation site (e.g., the plaque region on the periphery of the blood vessels and coronary arteries region).

Next, the CPU 11 performs a display image generation process (step 13). The CPU 11 generates a display image based on the region of interest set in the step 12. By way of example, if a pixel having a reference pixel value on a projection line of interest corresponds to a pixel in the region of the observation site, the CPU 11 generates a display image that allows the size of a lesion candidate region to be distinguishable, the lesion candidate region being adjacent to the region of the observation site. The reference pixel value may be, for instance, the maximum pixel value on the projection line of interest, the minimum pixel value on the projection line of interest, or a pixel value being the closest to a predetermined pixel value on the projection line of interest, or the like.

The display image generating process is different in each of the embodiments, and details thereof will be explained later. In each of the embodiments, an explanations will be made, using an example that the reference pixel value corresponds to the maximum pixel value on the projection line of interest. This is because, typically, the maximum intensity projection (MIP) is employed for conducting a diagnosis of blood vessels in many cases. It is to be noted that for conducting a diagnosis of bronchial tube, the minimum intensity projection (MINIP), or the like, may be employed in some cases. Therefore, if the objection target is a bronchial tube, it is possible to assume the reference pixel value as the minimum pixel value on the projection line of interest.

Next, the CPU 11 performs the image displaying process (step 14). The CPU 11 displays the display image generated in the step 13, on the display 18 via the display memory 17. It is also possible for the CPU 11 to display only the display image viewed from a certain projection direction. Alternatively, the CPU 11 may display simultaneously the display images viewed from predetermined multiple projection directions. Further alternatively, the CPU 11 may display the display images viewed from predetermined multiple projection directions sequentially in temporal order. It is to be noted that the present invention as described below enables only one display image to be sufficient for displaying information that is necessary for the diagnosis.

First Embodiment

With reference to the figures from FIG. 3 to FIG. 7C, the first embodiment of the present invention will be explained. In the first embodiment, the CPU 11 in the medical image display device 1 sets a projected pixel value, by using a distance (a vascular diameter) of the region of the observation site (blood vessels and coronary arteries, etc.), and a distance of the region of adjacent lesion candidate (plaque, etc.), and generates a display image in the display image generating process of the step 13. More specifically, in the case where the pixel having a reference pixel value on the projection line of interest corresponds to the pixel in the observation site region, the CPU 11 determines a weight coefficient according to the size of the region of the adjacent lesion candidate on the projection line of interest, and sets as the projected pixel value, a value weighted the weight coefficient to the pixel value based on a group of pixels in the region of the adjacent lesion candidate on the projection line of interest, and the reference pixel value on the projection line of interest. In particular, the CPU 11 determines the weight coefficient, based on the number of pixels in the region of the adjacent lesion candidate on the projection line of interest, and the number of pixels in the observation site region including the reference pixel value on the projection line of interest.

Figure 3:
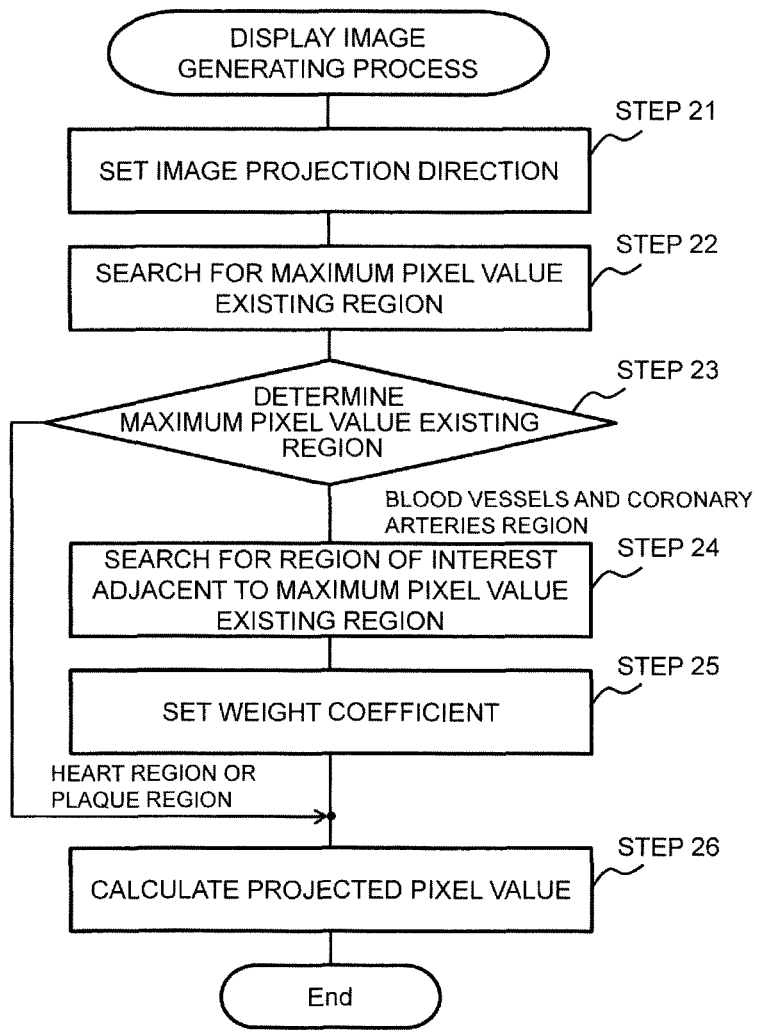
FIG. 3 is a flowchart illustrating a display image generating process in the first embodiment.
Figure 4:
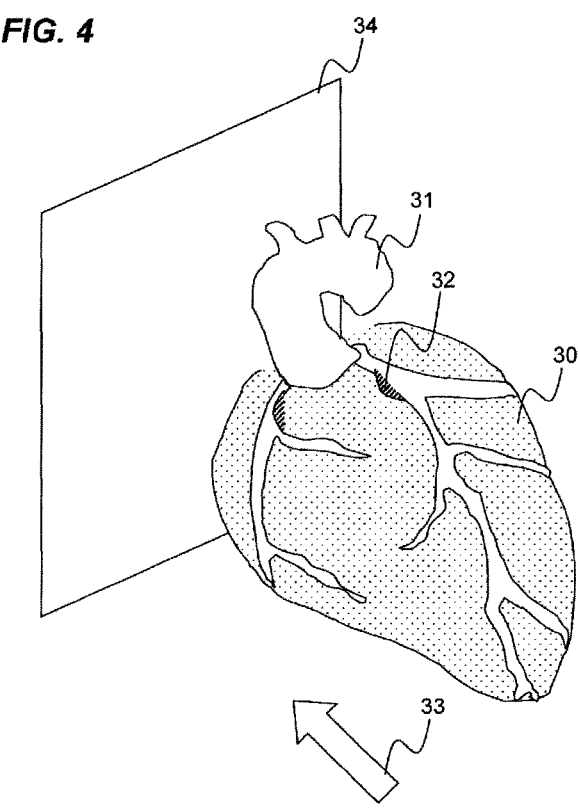
FIG. 4 is a schematic view for illustrating an image projection direction setting process.

As illustrated in FIG. 3, the CPU 11 of the medical image display device 1 performs an image projection direction setting process (step 21). With reference to FIG. 4, the image projection direction setting process will be explained.

FIG. 4 illustrates the region of interest that is set in the step 12. FIG. 4 illustrates the heart region 30, the blood vessels and coronary arteries region 31, and the plaque region 32, as the region of interest. When the operator indicates the direction in which the image is projected, via the input device, the CPU 11 sets the projection direction 33 and the projection plane 34, in response to the indication. The projection plane 34 is set in such a manner as perpendicular to the projection direction 33 being indicated, for each projection direction. By way of example, the operator may manipulate the mouse 13, the keyboard 14, or the like, so as to input a projection angle that defines the projection direction 33. In addition, according to a drag operation by using the mouse 13, the projection direction or the projection plane may be designated while turning it around. In addition, the CPU 11 may be allowed to set the projection angle being empirically-defined.

The projection angle may be defined, for example, by an azimuth that indicates an angle in the horizontal direction, and elevation and depression angles that indicate the angles in the vertical direction (an upward angle indicates the elevation angle, and a downward angle indicates the depression angle). Only one direction may be set as the projection direction 33 as shown in FIG. 4, but it is also possible to set multiple directions.

Figure 5A:
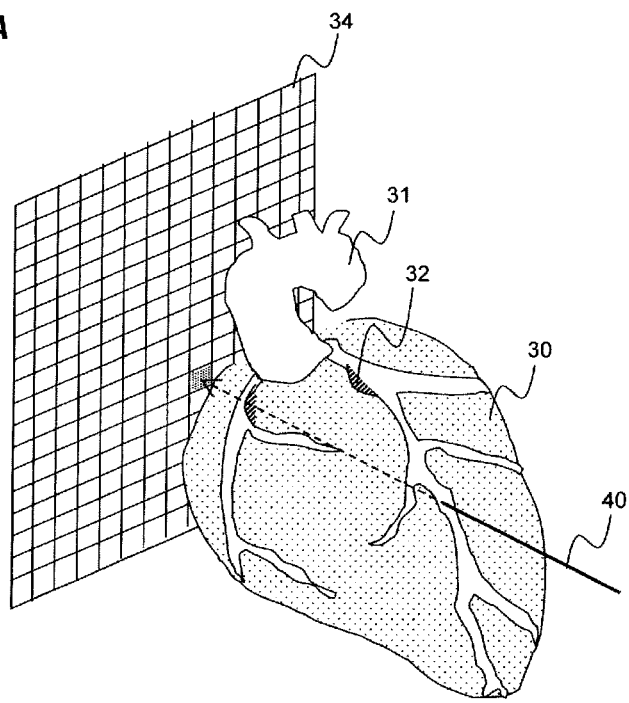
FIG. 5A is a schematic view for illustrating a searching process for a maximum pixel value existing region.

Here, the explanation turns back to FIG. 3. Next, the CPU 11 performs the maximum pixel value existing region searching process (step 22). The maximum pixel value existing region searching process will be explained, with reference to FIG. 5A and FIG. 5B. FIG. 5A illustrates a projection plane and a projection direction, and FIG. 5B illustrates a group of pixels which are taken out along the projection direction.

As illustrated in FIG. 5A, the CPU 11 sets the projection line 40 to each of the pixels on the projection plane 34 along the projection direction 33. The projection method may be perspective projection or parallel projection. In the case of perspective projection, it is possible to obtain a projected image being the same as the image that comes into human eyes. As for the case of the parallel projection, since the projection lines are parallel to each other, it is possible to simplify the process performed by the CPU 11.

Figure 5B:
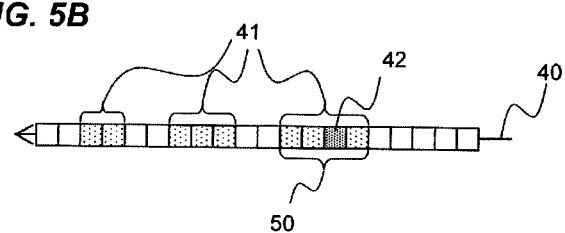
FIG. 5B is a schematic view for illustrating a searching process for a maximum pixel value existing region.

As illustrated in FIG. 5B, multiple pixels 41 of the region of interest are included in the projection line 40, the region of interest being set in the step 12. The CPU 11 searches the multiple pixels 41 of the region of interest, for a pixel 42 having the maximum pixel value $I_C$ (hereinafter, referred to as a "maximum value pixel 42"). Then, the CPU 11 specifies the region of interest 50 including the maximum value pixel 42 (hereinafter, referred to as a "maximum pixel value existing region 50"). The maximum pixel value existing region 50 may correspond to any of the heart region 30, the blood vessels and coronary arteries region 31, or the plaque region 32, which is the region of interest being set in the step 12.

Here, the explanation turns back to FIG. 3. Next, the CPU 11 performs a maximum pixel value existing region determining process (step 23). The CPU 11 determines to which region the maximum pixel value existing region 50 identified in the step 22 corresponds, among the heart region 30, the blood vessels and coronary arteries region 31, or the plaque region 32. If it corresponds to the blood vessels and coronary arteries region 31 being the observation site region (the "blood vessels and coronary arteries region" in the step 23), the process proceeds to the step 24. If it corresponds to the other regions, the heart region 30 or the plaque region 32 (the "heart region or the plaque region" in the step 23), the process proceeds to the step 26.

If the maximum pixel value existing region 50 corresponds to the blood vessels and coronary arteries region 31 being the observation site region (the "blood vessels and coronary arteries region" in the step 23), the CPU 11 performs a region of interest searching process for searching for a region of interest that is adjacent to the maximum pixel value existing region (step 24). The searching process for a region of interest that is adjacent to the maximum pixel value existing region will be explained with reference to FIG. 6.

Figure 6:
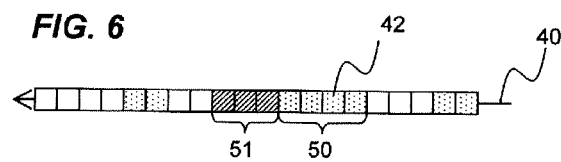
FIG. 6 is a schematic view for illustrating a searching process for a region of interest that is adjacent to the maximum pixel value existing region.

As illustrated in FIG. 6, if there exists a region of interest adjacent to the maximum pixel value existing region 50, the CPU 11 specifies to which region the region 51 (hereinafter, referred to as "adjacent region of interest 51") corresponds; the heart region 30 or the plaque region 32. In the example as illustrated in FIG. 6, the adjacent region of interest 51 exists only on the backside with respect to the projection direction of the projection line 40 (on the left side in FIG. 6).

In addition to the example as illustrated in FIG. 6, it is also conceivable that adjacent region of interest 51 may exist only on the front side with respect to the projection direction of the projection line 40 (on the right side in FIG. 6), or the adjacent regions may exist on both sides, backside and front side. If the adjacent region of interest 51 exists only on the front side, the CPU 11 identifies the adjacent region of interest 51, similar to the case where it exists only on the backside. If the adjacent regions of interest 51 exist on both sides, backside and front side, the CPU 11 specifies the regions being combined as the adjacent region of interest 51, when both regions are the same region of interest (e.g., both regions correspond to the plaque region 32). If the adjacent regions of interest 51 exist on both sides, backside and front side, the CPU 11 places higher priority on the plaque region 32 to be identified as the adjacent region of interest 51, when those regions of interest are different from each other (e.g., the heart region 30 and the plaque region 32).

Here, the explanation turns back to FIG. 3. Next, the CPU 11 performs the weight coefficient setting process (step 25). Firstly, the CPU 11 calculates a number of pixels $N_C$ as the distance of the maximum pixel value existing region 50 in the projection direction on the projection line 40. Next, the CPU 11 calculates a number of pixels $N_P$ as the distance of the adjacent region of interest 51 in the projection direction on the projection line 40. Here, the CPU 11 sets $N_P=0$, when the adjacent region of interest 51 corresponds to a region other than the lesion candidate region, that is, the heart region 30 or the blood vessels and coronary arteries region 31. In other words, the CPU 11 counts the number of pixels $N_P$, only in the case where the adjacent region of interest 51 corresponds to the lesion candidate region, that is, the plaque region 32. Then, the CPU 11 sets the weight coefficient $W_C$ in association with the maximum pixel value existing region 50, and the weight coefficient $W_P$ in association with the adjacent region of interest 51, according to the following formulas:

$$W_C = \frac{N_C}{N_C + N_P} \quad (1)$$

$$W_P = \frac{N_P}{N_C + N_P} \quad (2)$$

As described above, the CPU 11 counts the number of pixels $N_P$ only when the adjacent region of interest 51 corresponds to the lesion candidate region (here, the plaque region 32). Therefore, when the adjacent region of interest 51 corresponds to the lesion candidate region (plaque region 32), $0<W_C, W_P<1$, and when the adjacent region of interest 51 corresponds to the other regions (here, the heart region 30 or the blood vessels and coronary arteries region 31), $W_C=1$ and $W_P=0$.

Next, the CPU 11 performs the projected pixel value calculating process (step 26). When the maximum pixel value existing region 50 corresponds to a region other than the observation site region (here, the heart region 30 or the plaque region 32), the CPU 11 assumes the maximum pixel value $I_C$ specified in the step 22 as the projected pixel value on the projection line 40. When the maximum pixel value existing region 50 corresponds to the observation site region (here, the blood vessels and coronary arteries region 31), the CPU 11 sets the projected pixel value of the projection line 40, by using the weight coefficients calculated in the formula (1) and the formula (2), according to the following formula.

$$I = W_C I_C + W_P I_P \qquad (3)$$

Here, $I_C$ represents the largest pixel value in all of the projection lines 40. As for $I_P$, it represents a maximum pixel value, a minimum pixel value, an average pixel value, or the like, of the adjacent region of interest 51 on the projection line 40.

The CPU 11 executes the processes from the step 22 to the step 26 on all the pixels on the projection plane 34, in other words, for all the projection lines 40, thereby generating a display image.

Figure 7A:
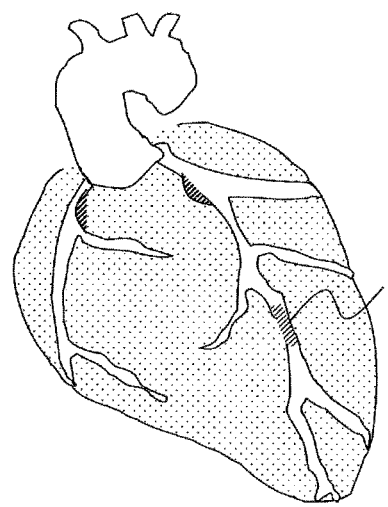
FIG. 7A illustrates an example of the display image in the first embodiment.
Figure 7B:
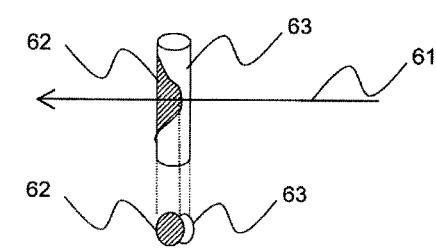
FIG. 7B illustrates an example of the display image in the first embodiment.
Figure 7C:
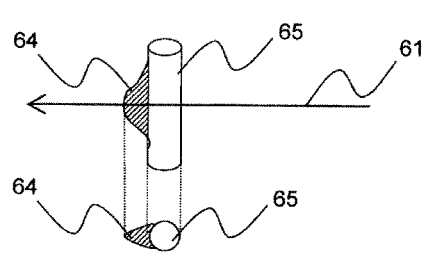
FIG. 7C illustrates an example of the display image in the first embodiment.

FIG. 7A illustrates one example of the display image generated by the first embodiment. FIG. 7B and FIG. 7C are enlarged views, each showing the site 60 as illustrated in FIG. 7A. Each of FIG. 7B and FIG. 7C illustrates a schematic perspective view of the blood vessels and coronary arteries 63, 65 relating to the site 60, and a schematic cross-sectional view (the cross section including the projection line 61) of the blood vessels and coronary arteries 63, 65.

As illustrated in FIG. 7B and FIG. 7C, in the case where the eccentric plaque 62, 64 exists in the direction along the projection line 61 (in the depth direction of the display image), a pixel value associated with the blood vessels and coronary arteries 63, 65 is displayed as it is, in the image generated by a conventional maximum pixel value projecting method, and therefore, in some cases, the existence of the eccentric plaque 62, 64 is not reflected on the image.

On the other hand, according to the first embodiment, the position where the eccentric plaque 62, 64 exists, being adjacent to the blood vessels and coronary arteries 63, 65 is reflected as a portion where the pixel value becomes lowered in the blood vessels and coronary arteries 63, 65. In other words, since the formula (3); the projected pixel value $I = W_C \cdot I_C + W_P \cdot I_P < (W_C + W_P) I_C = I_C$ is established, the projected pixel value I of the formula (3) becomes a value that is constantly smaller than the maximum pixel value $I_C$. Therefore, the pixel value of the pixels of the blood vessels and coronary arteries 63 at the positions where the eccentric plaque 62, 64 exists in such a manner as adjacent to the blood vessels and coronary arteries 63 becomes lower than the pixel value of the pixels on the periphery thereof.

In the example as shown in FIG. 7B, there is found a sharp decline of the pixel value at the position where the adjacent eccentric plaque 62 exists, relative to the pixel value on the periphery thereof. This is because, the distance (the number of pixels) of the blood vessels and coronary arteries 63 on the projection line 61 becomes shorter relative to the distance (number of pixels) of the adjacent eccentric plaque 62 on the projection line 61, and the projected pixel value I of the projection line 61 calculated according to the formula (3) becomes an extremely small value. As shown in FIG. 7B, it would be highly probable that the portion of the pixels within the observation site region where the pixel value becomes significantly lower relative to the pixel value on the periphery thereof, indicates an abnormality of the vascular constriction type.

Further in the example of FIG. 7C, the pixel value at the position where the eccentric plaque 64 exists adjacently is lowered moderately from the pixel values on the periphery. This is because, the distance (number of pixels) of the blood vessels and coronary arteries 65 on the projection line 61 becomes longer relative to the distance (number of pixels) of the adjacent eccentric plaque 64 on the projection line 61, and the projected pixel value I of the projection line 61 according to the formula (3) does not become an extremely small value. As shown in FIG. 7C, it would be highly probable that the portion of the pixels within the observation site region, where the pixel value is lowered moderately from the pixel value on the periphery thereof, indicates an abnormality of the type that plaque expands outwardly from the blood vessel, without changing the vascular diameter (referred to as compensatory enlargement or the like).

As discussed above, the medical image display device of the present embodiment is provided with a region of interest setter for setting a first region of interest being a region of an observation site in volume data, and a second region of interest being a lesion candidate region relating to the observation site, a display image generator for generating a display image that allows the size of an adjacent second region of interest to be distinguishable, being the second region of interest adjacent to the first region of interest on a projection line of interest, when a pixel having a reference pixel value on the projection line of interest corresponds to a pixel of the first region of interest, and a display unit for displaying the display image. On this occasion, when the pixel having the reference pixel value on the projection line of interest corresponds to the pixel of the first region of interest, the display image generator may determine a weight coefficient according to the size of the adjacent second region of interest, and set a value as a projected pixel value for the projection line of interest, the value being weighted the weight coefficient to the pixel value based on a group of pixels in the adjacent second region of interest and the reference pixel value on the projection line of interest. It is also possible for the display image generator to determine the weight coefficient, based on the number of pixels in the adjacent second region of interest and the number of pixels in the first region of interest including the reference pixel value.

Therefore, according to the first embodiment, it is possible to reflect on one display image, whether or not a lesion candidate exists and the position thereof, and information based on the shape of the region of the hollow organ and the periphery thereof, and sufficiently display information necessary for diagnosis, thereby supporting that the diagnosis without error is conducted in a short period of time. In particular, in the first embodiment, the position where the lesion candidate exists is reflected on the image as a portion where the pixel value is reduced in the hollow organ. Furthermore, the information based on the shape of the hollow organ and the periphery thereof is reflected as a difference in the degree of the pixel value reduction.

It is to be noted that $I_P$ in the formula (3) represents any of the following; a maximum pixel value, a minimum pixel value, an average pixel value, and the like, of the adjacent region of interest 51 on the projection line 40. By way of example, as explained above, when $I_C$ in the formula (3) is the largest pixel value of all of the projection lines 40 identified in the step 22, it is desirable that $I_P$ in the formula (3) is a minimum pixel value or an average pixel value of the adjacent region of interest 51 on the projection line 40. In other words, in the case where the reference pixel value is the maximum pixel value on the projection line of interest, it is desirable that the CPU 11 substitutes the average pixel value or the minimum pixel value of the adjacent region of interest on the projection line of interest into $I_P$ in the formula (3), thereby setting the projected pixel value. Accordingly, a difference between the pixel value of the pixel where the lesion candidate exists, and the pixel value of the region on the peripheral thereof being the observation site (blood vessels and coronary arteries, etc.) becomes larger, and this facilitates visual recognition of the position of the lesion candidate.

By way of example, in the case where the reference pixel value is the minimum pixel value on the projection line of interest, it is desirable that the CPU 11 substitutes the average value or the maximum pixel value of the adjacent region of interest on the projection line of interest, into $I_P$ in the formula (3), thereby setting the projected pixel value. Accordingly, a difference between the pixel value of the pixel where the lesion candidate exists, and the pixel value of the region on the peripheral thereof being the observation site (blood vessels and coronary arteries, etc.) becomes larger, and this facilitates visual recognition of the position of the lesion candidate.

Second Embodiment

With reference to FIG. 8, FIG. 9A, FIG. 9B, and FIG. 9C, the second embodiment of the present invention will be explained. In the second embodiment, the CPU 11 of the medical image display device 1 sets a color value in the display image generation process of the step 13, by using the change in the distance (the vascular diameter) of the region of the observation site (blood vessels and coronary arteries, etc.), the distance of the region of the adjacent lesion candidate (plaque, etc.), and the distance (the vascular diameter) of the peripheral observation site region. Then, the CPU 11 displays an image obtained by superimposing the color value on the display image in the image displaying process of the step 14. More specifically, the CPU 11 sets the reference pixel value on the projection line of interest, as a projected pixel value for the projection line of interest. When the pixel having the reference pixel value on the projection line of interest corresponds to a pixel in the region of the observation site (blood vessels and coronary arteries, etc.), the CPU 11 determines a color value of a color attribute being different from that of the projected pixel value according to the size of the region of the adjacent lesion candidate (plaque, etc.) on the projection line of interest. The color attribute may include, for instance, a hue, chroma, brightness, a degree of transparency, etc. In particular, the CPU 11 determines the color value, based on the number of pixels in the observation site region that is positioned on the projection line of interest including a pixel having the reference pixel value on the projection line of interest, and the number of pixels in the observation site region that is positioned on a projection line being adjacent to the projection line of interest, and that is positioned on the periphery of the pixel having the reference pixel value.

As shown in FIG. 8, the CPU 11 of the medical image display device 1 performs the image projection direction setting process (step 31). The image projection direction setting process is similar to the process of the step 21 as illustrated in FIG. 3. Next, the CPU 11 performs the maximum pixel value existing region searching process (step 32). The maximum pixel value existing region searching process is similar to the process of the step 22 as illustrated in FIG. 3.

Next, the CPU 11 performs the maximum pixel value existing region determining process (step 33). The CPU 11 determines to which region the maximum pixel value existing region 50 identified in the step 32 corresponds, among the heart region 30, the blood vessels and coronary arteries region 31, or the plague region 32. Then, if it corresponds to the blood vessels and coronary arteries region 31 being the observation site region (the "blood vessels and coronary arteries region" in the step 33), the process proceeds to the step 34, and if it corresponds to the other regions, the heart region 30 or the plaque region 32 (the "heart region" or "plaque region" in the step 33), the process proceeds to the step 37.

In the case where the maximum pixel value existing region 50 corresponds to the blood vessels and coronary arteries region 31 being the observation site region (the "blood vessels and coronary arteries region" in the step 33), the CPU 11 performs a region of interest searching process for searching for the region of interest that is adjacent to the maximum pixel value existing region (step 34). The region of interest searching process for searching for the region of interest that is adjacent to the maximum pixel value existing region is similar to the process of the step 24 in FIG. 3.

Next, the CPU 11 performs an observation site region distance calculating process (step 35). The CPU 11 calculates a distance (here, the number of pixels) of the maximum pixel value existing region 50 on the projection line of interest 40, and a distance (here, the number of pixels) of the maximum pixel value existing region 50 on a projection line on the periphery of the projection line of interest 40. In the case where the maximum pixel value existing region 50 corresponds to the blood vessels and coronary arteries region 31, the distance of the maximum pixel value existing region 50 becomes a diameter of the blood vessels and coronary arteries. A range for the projection line on the periphery of the projection line of interest 40 is predetermined, which is targeted for calculating the distance of the maximum pixel value existing region 50.

Next, the CPU 11 performs a color value calculating process (step 36). The CPU 11 firstly determines based on the calculation result of the step 35, whether or not the distance of the observation site region (here, the diameter of the blood vessels and coronary arteries) at the position of interest is reduced, relative to the distance of the peripheral observation site region (the diameter of the blood vessels and coronary arteries). Next, in the case where the adjacent region of interest 51 corresponds to the lesion candidate region (the plague), the CPU 11 calculates the number of pixels $N_P$ in the adjacent region of interest 51 (distance in the projection line direction of the adjacent region of interest 51) on the projection line 40, and converts the result into a color value by using a color table. Here, in the color table, 256 gradations of color tones are arranged in the order of red, green, and blue, for instance, and in the case where the adjacent region of interest 51 does not exist, or the adjacent region of interest 51 is not the lesion candidate region (plaque), a color value is set to be green, which is an intermediate color. Then, when the distance of the observation site region (the diameter of blood vessels and coronary arteries) at the position of interest is reduced relative to the distance of the peripheral observation site region (the diameter of the blood vessels and coronary arteries diameter), the CPU 11 uses a domain from green to red in the color table, and as the number of pixels $N_P$ in the lesion candidate region (the distance of the plaque region) becomes larger, the CPU 11 uses a color being closer to red. On the other hand, when the distance in the observation site region (the diameter of blood vessels and coronary arteries) at the position of interest is not reduced relative to the distance of the peripheral observation site region (the diameter of the blood vessels and coronary arteries), the CPU 11 uses a domain from green to blue in the color table, and as the number of pixels $N_P$ in the lesion candidate region (the distance of the plaque region) becomes larger, the CPU 11 uses a color being closer to blue.

Next, the CPU 11 performs the projected pixel value calculating process (step 37). The CPU 11 assumes the maximum pixel value $I_C$ that is calculated in the step 32 as the projected pixel value on the projection line 40. Next, the CPU 11 establishes association between the projected pixel value being set in the step 37 and the color value that is set in the step 36, and the data is stored in the main memory 15, or the like (step 38). In the second embodiment, the display image based on the projected pixel value allows displaying of an image where the color value is superimposed thereon, and by a difference of the color value gradations, it is possible to visibly recognize whether or not the vascular diameter of the blood vessels and coronary arteries is reduced at the position of interest.

The CPU 11 executes the processing from the step 32 to the step 38 on all of the pixels on the projection plane 34, in other words, on all the projection lines 40, thereby generating a display image.

Figure 9A:
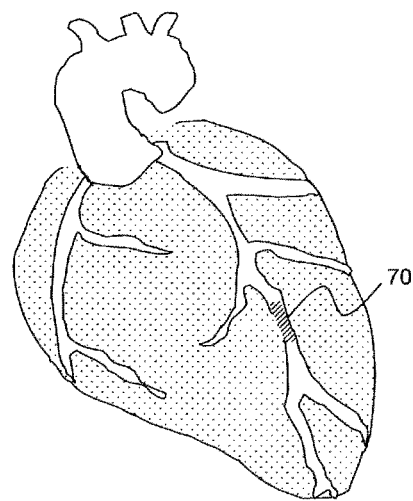
FIG. 9A illustrates an example of the display image in the second embodiment.
Figure 9B:
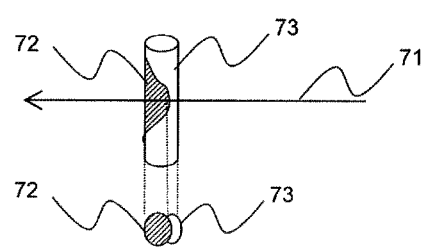
FIG. 9B illustrates an example of the display image in the second embodiment.
Figure 9C:
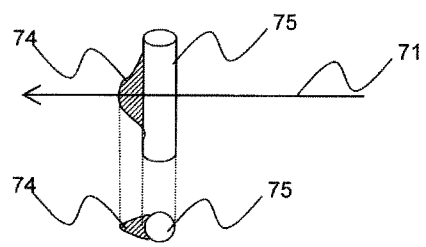
FIG. 9C illustrates an example of the display image in the second embodiment.

FIG. 9A illustrates one example of the display image that is generated according to the second embodiment. FIG. 9B and FIG. 9C are enlarged views of the site 70 as shown in FIG. 9A. FIG. 9B and FIG. 9C illustrate, a schematic perspective view of the blood vessels and coronary arteries 73, 75 relating to the site 70, and a schematic cross sectional view (the cross-section surface includes the projection line 71) of the blood vessels and coronary arteries 73, 75. It is to be noted that color values are not illustrated due to the restriction of drawings in patent applications.

As shown in FIG. 9B and FIG. 9C, in the case where the eccentric plaque 72, 74 exists in the direction along the projection line 71 (in the depth direction of the display image), the pixel value associated with the blood vessels and coronary arteries 73, 75 is displayed as it is, in an image generated by a conventional maximum pixel value projecting method. Therefore, in some cases, existence of the eccentric plaque 72, 74 is not reflected on the image.

On the other hand, according to the second embodiment, the color value is superimposed on the blood vessels and coronary arteries 73, 75 at the position where the eccentric plaque 72, 74 exists, and therefore it is possible to visibly recognize the existence of the eccentric plaque 72, 74. In the example of FIG. 9B, the color value closed to red is superimposed on the position where the eccentric plaque 72 exists. This is because, the diameter of the blood vessels and coronary arteries (the distance of the blood vessels and coronary arteries 73 on the projection line 71) at the position of interest is reduced relative to the diameter of the blood vessels and coronary arteries on the peripheral position (the distance of the blood vessels and coronary arteries 73 on a projection line on the periphery of the projection line 71). As shown in FIG. 9B, it would be highly probable that the portion on which the color value close to red is superimposed indicates an abnormality of the vascular constriction type.

In the example of FIG. 9C, the color value close to blue is superimposed on the position where the eccentric plaque 74 exists. This is because, the diameter of the blood vessels and coronary arteries at the position of interest (the distance of the blood vessels and coronary arteries 75 on the projection line 71) is approximately the same as the diameter of the blood vessels and coronary arteries at the peripheral position (the distance of the blood vessels and coronary arteries 75 on a projection line on the periphery of the projection line 71). As shown in FIG. 9C, it would be highly probable that the portion on which the color value close to blue is superimposed, indicates an abnormality of the type that plaque expands outwardly from the blood vessel without changing the vascular diameter (referred to as compensatory enlargement or the like).

As discussed above, the medical image display device of the present embodiment is provided with a region of interest setter for setting a first region of interest being a region of an observation site in volume data, and a second region of interest being a lesion candidate region relating to the observation site, a display image generator for generating a display image that allows a size of an adjacent second region of interest to be distinguishable, being the second region of interest adjacent to the first region of interest on a projection line of interest, when a pixel having a reference pixel value on the projection line of interest corresponds to a pixel of the first region of interest, and a display unit for displaying the display image. On this occasion, the display image generator sets the reference pixel value on the projection line of interest as a projected pixel value for the projection line of interest, and when the pixel having the reference pixel value on the projection line of interest corresponds to the pixel of the first region of interest, the display image generator may determine a color value of a color attribute being different from that of the projected pixel value, depending on the size of the adjacent second region of interest, and the display unit may display an image obtained by superimposing the color value on the display image. It is further possible for the display image generator to determine the color value, based on the number of pixels of the first region of interest being a region positioned on the projection line of interest including a pixel having the reference pixel value, and the number of pixels of the first region of interest being a region that is positioned on a projection line being adjacent to the projection line of interest, and that is positioned on the periphery of the pixel having the reference pixel value.

Therefore, according to the second embodiment, it is possible to reflect on one display image, whether or not a lesion candidate exists and where it exists, and information based on the shape of the hollow organ and the peripheral region thereof, and sufficiently display information necessary for diagnosis, thereby supporting that the diagnosis without error is conducted in a short period of time. Particularly, in the second embodiment, the color value is superimposed on the position where the lesion candidate exists. In addition, the information based on the shape of the hollow organ and the region on the periphery thereof is reflected as a difference in gradations of the color value.

Third Embodiment

With reference to FIG. 10, the third embodiment of the present invention will be explained. In the third embodiment, the CPU 11 of the medical image display device 1 converts into a color value, a ratio of the pixel value corresponding to a tissue of interest (e.g., lipid) within the region of the lesion candidate (plaque, etc.), for the display image that is generated in the first embodiment, in the display image generation process of the step 13, and displays an image obtained by superimposing the color value on the display image in the image displaying process in the step 14. More specifically, in the third embodiment, the CPU 11 calculates an index value indicating a ratio of the pixels that represent the tissue of interest in the adjacent lesion candidate region on the projection line of interest, and according to the index value, the CPU 11 determines a color value of a color attribute that is different from that of the projected pixel value.

As shown in FIG. 10, the CPU 11 of the medical image display device 1 performs the image projection direction setting process (step 41). The image projection direction setting process is similar to the process of the step 21 in FIG. 3. Next, the CPU 11 performs the maximum pixel value existing region searching process (step 42). The maximum pixel value existing region searching process is similar to the process of the step 22 in FIG. 3.

Next, the CPU 11 performs the maximum pixel value existing region determining process (step 43). The CPU 11 determines to which region the maximum pixel value existing region 50 identified in the step 42 corresponds, among the heart region 30, the blood vessels and coronary arteries region 31, or the plaque region 32. Then, if it corresponds to the blood vessels and coronary arteries region 31 being the region of the observation site (the "blood vessels and coronary arteries region" in the step 43), the process proceeds to the step 44, and if it corresponds to the other region, the heart region 30 or the plaque region 32 (the "heart region" or the "plaque region" in the step 43), the process proceeds to the step 46.

In the case where the maximum pixel value existing region 50 corresponds to the blood vessels and coronary arteries region 31 being the region of the observation site (the "blood vessels and coronary arteries region" in the step 43), the CPU 11 performs the region of interest searching process for searching for the region of interest that is adjacent to the maximum pixel value existing region (step 44). The region of interest searching process for searching for the region of interest that is adjacent to the maximum pixel value existing region is similar to the step 24 in FIG. 3.

Next, the CPU 11 performs a weight coefficient setting process (step 45). The weight coefficient setting process is similar to the process of the step 25 in FIG. 3. Next, the CPU 11 performs the projected pixel value calculating process (step 46). The projected pixel value calculating process is similar to the process of the step 26 in FIG. 3.

Next, the CPU 11 performs the color value setting process (step 47). The CPU 11 calculates a ratio of the tissue of interest (here, lipid) in the lesion candidate region (here, the plaque region 32). More specifically, the CPU 11 extracts pixels that represent the lipid, according to a threshold process using pixel value information such as a CT value, and calculates a ratio of the pixels representing the lipid in the plaque region 32. Then, the CPU 11 converts the ratio of the lipid into the color value, by using a color table.

Next, the CPU 11 establishes association between the projected pixel value set in the step 46 with the color value set in the step 47, and stores the result in the main memory 15, or the like (step 48). In the third embodiment, the display image based on the projected pixel value is superimposed the color value and displayed, and according to the difference in gradations of the color value, it is possible to visibly recognize whether or not the plaque is rich in lipid.

The CPU 11 executes the processes from the step 42 to the step 48 on all the pixels on the projection plane 34, in other words, on all the projection lines 40, thereby generating a display image.

As discussed above, the medical image display device of the present embodiment is provided with a region of interest setter for setting a first region of interest being a region of an observation site in volume data, and a second region of interest being a lesion candidate region relating to the observation site, a display image generator for generating a display image that allows a size of an adjacent second region of interest to be distinguishable, being the second region of interest adjacent to the first region of interest on a projection line of interest, when a pixel having a reference pixel value on the projection line of interest corresponds to a pixel of the first region of interest, and a display unit for displaying the display image. On this occasion, when the pixel having the reference pixel value on the projection line of interest corresponds to the pixel of the first region of interest, the display image generator may determine a weight coefficient according to the size of the adjacent second region of interest, and set a value as a projected pixel value for the projection line of interest, the value being weighted the weight coefficient to the pixel value based on a group of pixels in the adjacent second region of interest and the reference pixel value on the projection line of interest. In addition, the display image generator may calculate a first index value indicating a ratio of the pixels representing a tissue of interest in the adjacent second region of interest, and determine a color value of a color attribute that is different from that of the projected pixel value, according to the first index value, and the display unit displays an image obtained by superimposing the color value on the display image.

Therefore, according to the third embodiment, it is possible to reflect on one display image, information relating to whether or not a lesion candidate exists and where it exists, information relating to the composition, and information based on the shape of the hollow organ and the peripheral region thereof, and sufficiently display information necessary for diagnosis, thereby supporting that the diagnosis without error is conducted in a short period of time. Particularly, in the third embodiment, the position where the lesion candidate exists is reflected as a portion where the pixel value is reduced within the hollow organ. In addition, the information based on the shape of the hollow organ and the region in the periphery thereof is reflected as a difference in a degree of reduction of the pixel value. Furthermore, the information relating to the composition of the lesion candidate is reflected as a difference in gradations of the color value.

Fourth Embodiment

Figure 12:
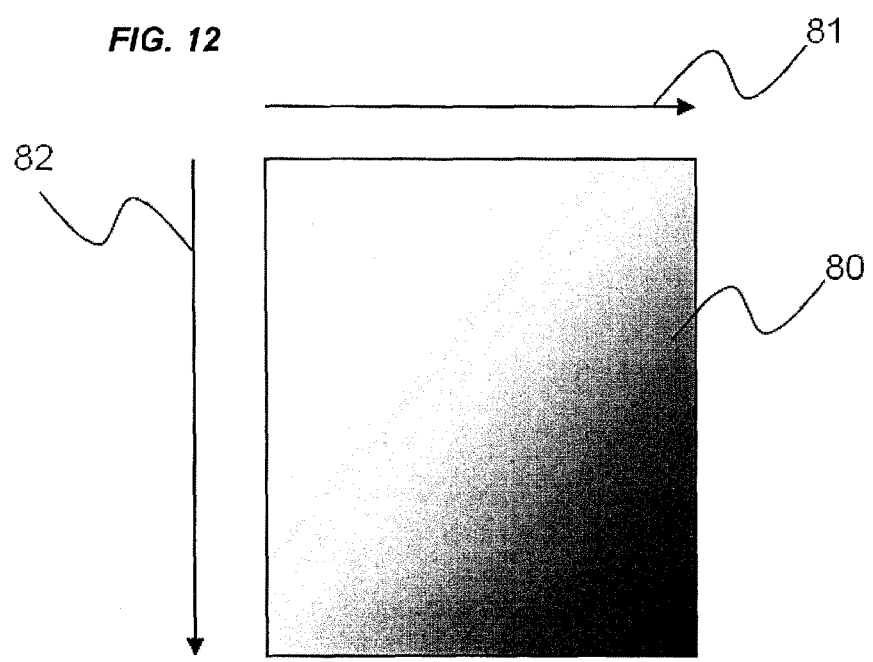
FIG. 12 illustrates an example of a two-dimensional color map.

With reference to FIG. 11 and FIG. 12, the fourth embodiment of the present invention is applied will be explained. In the fourth embodiment, the CPU 11 of the medical image display device 1 sets a color value based on two indexes; a ratio of the pixels corresponding to a tissue of interest (e.g., lipid) within the region of the lesion candidate (plaque, etc.), and the ratio between the diameter of the observation site at a point of interest and the diameter of the observation site on the periphery thereof the blood vessels and coronary arteries, etc.), in the display image generation process of the step 13. Then, the CPU 11 displays an image obtained by superimposing the color value on the display image in the image displaying process of the step 14. More specifically, the CPU 11 calculates an index value indicating the ratio of the pixels representing the tissue of interest in the adjacent lesion candidate region on the projection line of interest, and further calculates an index value indicating a ratio between the number of pixels in the observation site region being a region positioned cn the projection line of interest, and including the pixel having the reference pixel value, and the number of pixels in the observation site region being a region that is positioned on a projection line being adjacent to the projection line of interest, and a region that is positioned on the periphery of the pixel having the reference pixel value. Then, according to those two index values, a color value in a color attribute which is different from that of the projected pixel value is determined.

As show in FIG. 11, the CPU 11 of the medical image display device 1 performs the image projection direction setting process (step 51). The image projection direction setting process is similar to the step 21 as shown in FIG. 3. Next, the CPU 11 performs the maximum pixel value existing region searching process (step 52). The maximum pixel value existing region searching process is similar to the step 22 as shown in FIG. 3.

Next, the CPU 11 performs the maximum pixel value existing region determining process (step 53). The CPU 11 determines to which region the maximum pixel value existing region 50 identified in the step 52 corresponds, among the heart region 30, the blood vessels and coronary arteries region 31, or the plaque region 32. When it corresponds to the blood vessels and coronary arteries region 31 being the observation site region (the "blood vessels and coronary arteries region" in the step 53), the process proceeds to the step 54, and when it corresponds to the other regions, the heart region 30 or the plaque region 32 (the "heart region" or the "plaque region" in the step 53), the process proceeds to the step 58.

When the maximum pixel value existing region 50 corresponds to the blood vessels and coronary arteries region 31 being the observation site region (the "blood vessels and coronary arteries region" in the step 53), the CPU 11 performs a region of interest searching process for searching for the region of interest that is adjacent to the maximum pixel value existing region (step 54). The region of interest searching process for searching for the region of interest that is adjacent to the maximum pixel value existing region is similar to the step 24 of FIG. 3.

Next, the CPU 11 performs the weight coefficient setting process (step 55). The weight coefficient setting process is similar to the step 25 of FIG. 3. Next, the CPU 11 performs an observation site region distance calculating process (step 56). The observation site region distance calculating process is similar to the step 35 of FIG. 8.

Next, the CPU 11 performs the observation site region distance ratio calculating process (step 57). The CPU 11 calculates, based on the result of the step 56, a ratio of the distance of the observation site region at the position of interest (here, the vascular diameter of the blood vessels and coronary arteries), to the distance of the observation site region (the diameter of the blood vessels and coronary arteries) at the peripheral position being calculated. By way of example, if the blood vessels and coronary arteries region 31 being the maximum pixel value existing region 50 corresponds to a constricted area, the ratio calculated in the step 57 becomes a small value. On the other hand, the blood vessels and coronary arteries region 31 being the maximum pixel value existing region 50 corresponds to a normal region, the ratio calculated in the step 57 becomes a value being close to 1.

Next, the CPU 11 performs the tissue of interest ratio calculating process (step 58). The tissue of interest ratio calculating process is similar to a part of the process of the step 47 in FIG. 10. In other words, according to the threshold process using the pixel value information such a CT value, for instance, the CPU 11 extracts pixels representing the tissue of interest (here, lipid), and calculates a ratio of the tissue of interest (lipid) in the lesion candidate region (here, the plaque region 32). Next, the CPU 11 performs the projected pixel value calculating process (step 59). The projected pixel value calculating process is similar to the process of the step 26 in FIG. 3.

Next, the CPU 11 performs the color value setting process (step 60). The CPU 11 sets a color value by using the color map, based on the ratio of the distance of the observation site region calculated in the step 57 (here, the ratio of the vascular diameter of the blood vessels and coronary arteries, i.e., the ratio of the vascular diameter of the blood vessels and coronary arteries at the position of interest, to the vascular diameter at the peripheral position), and the tissue of interest ratio (here, the lipid ratio) calculated in the step 58. With reference to FIG. 12, an explanation will be made as to the color map.

FIG. 12 illustrates a two-dimensional color map 80. In the two-dimensional color map 80, for example, the axis 81 represents the ratio of the vascular diameter of the blood vessels and coronary arteries, and the axis 82 represents the ratio of lipid. The CPU 11 sets the color value uniquely, based on the ratio of the vascular diameter of the blood vessels and coronary arteries and the ratio of lipid, according to the two-dimensional color map 80. In FIG. 12, it is converted into a gray-scale image due to the restriction of drawings in patent applications.

Next, the CPU 11 establishes association between the projected pixel value set in the step 59, with the color value set in the step 60, and stores the result in the main memory 15, and the like (step 61). In the fourth embodiment, the display image based on the projected pixel value is superimposed the color value and displayed, and according to a difference in gradations of the color value, it is possible to visibly recognize whether or not the vascular diameter of the blood vessels and coronary arteries at the position of interest is reduced, and whether or not the plaque is rich in lipid.

The CPU 11 executes the processes from the step 52 to the step 61 on all the pixels on the projection plane 34, in other words, on all of the projection lines 40, thereby generating the display image.

As discussed above, the medical image display device of the present embodiment is provided with a region of interest setter for setting a first region of interest being a region of an observation site in volume data, and a second region of interest being a lesion candidate region relating to the observation site, a display image generator for generating a display image that allows a size of an adjacent second region of interest to be distinguishable, being the second region of interest adjacent to the first region of interest on a projection line of interest, when a pixel having a reference pixel value on the projection line of interest corresponds to a pixel of the first region of interest, and a display unit for displaying the display image. On this occasion, when the pixel having the reference pixel value on the projection line of interest corresponds to the pixel of the first region of interest, the display image generator may determine a weight coefficient according to the size of the adjacent second region of interest, and set a value as a projected pixel value for the projection line of interest, the value being weighted the weight coefficient to the pixel value based on a group of pixels in the adjacent second region of interest and the reference pixel value on the projection line of interest. In addition, the display image generator may calculate a first index value indicating a ratio of the pixels representing the tissue of interest in the adjacent second region of interest, and further calculate a second index value indicating a ratio between the number of pixels in the first region of interest region being a region positioned on the projection line of interest, and including the pixel having the reference pixel value, and the number of pixels in the first region of interest being a region that is positioned on a projection line being adjacent to the projection line of interest, and a region that is positioned on the periphery of the pixel having the reference pixel value. According to the first index value and the second index value, a color value of a color attribute being different from that of the projected pixel value is determined, and the display unit displays an image obtained by superimposing the color value on the display image.

Therefore, according to the fourth embodiment, it is possible to reflect on one display image, information relating to whether or note lesion candidate exists and where it exists, information relating to the composition thereof, and information based on the shape of the hollow organ and the peripheral region thereof, and sufficiently display information necessary for diagnosis, thereby supporting that the diagnosis without error is conducted in a short period of time. Particularly, in the fourth embodiment, the position where the lesion candidate exists is reflected as a portion where the number of pixels is reduced within the hollow organ. In addition, the information based on the shape of the hollow organ and the peripheral region thereof is reflected as a difference in the degree of reduction of the number of pixels. Furthermore, two types of information relating the composition of the lesion candidate are reflected as a difference in gradations of the color value.

With reference to the accompanying drawings, preferred embodiments of the image display device such as the medical image display device relating to the present invention have been explained, but the present invention is not limited to those examples. Obviously, those skilled in the art may readily appreciate that changes and various modifications are possible within the scope of the technical ideas disclosed by the present application, and accordingly, all such changes and modifications are intended to be included within the scope of the present invention.

EXPLANATION OF REFERENCES

1: medical image display device, 30: heart region, 31: blood vessels and coronary arteries region, 32: plaque region, 33: projection direction, 34: projection plane, 40, 61, 71: projection line, 41: pixels in the region of interest, 42: pixel having a maximum pixel value, 50: maximum pixel value existing region, 51: adjacent region of interest, 60, 70: site, 62, 64, 72, 74: eccentric plaque, 63, 65, 73, 75: blood vessels and coronary arteries, 80: two-dimensional color map

What is claimed is:

1. A medical image display device comprising,
a region of interest setter for setting a first region of interest being a region of an observation site in volume data, and a second region of interest being a lesion candidate region relating to the observation site,
a display image generator for generating a display image that allows a size of an adjacent region of interest, adjacent to the first region of interest on a projection line of interest, to be distinguishable, when a pixel having a reference pixel value on the projection line of interest corresponds to a pixel of the first region of interest and the adjacent region of interest is the second region, and
a display unit for displaying the display image, wherein
when the pixel having the reference pixel value on the projection line of interest corresponds to the pixel of the first region of interest, the display image generator determines a weight coefficient according to the size of the adjacent region of interest, and sets a value as a projected pixel value for the projection line of interest, the value being weighted the weight coefficient to a pixel value based on a group of pixels in the adjacent region of interest and the reference pixel value on the projection line of interest.

2. The medical image display device according to claim 1, wherein the display generator determines the weight coefficient based on a number of pixels in the adjacent region of interest and a number of pixels in the first region of interest including the reference pixel value.

3. A medical image display device comprising,
a region of interest setter for setting a first region of interest being a region of an observation site in volume data, and a second region of interest being a lesion candidate region relating to the observation site,
a display image generator for generating a display image that allows a size of an adjacent region of interest, adjacent to the first region of interest on a projection line of interest, to be distinguishable, when a pixel having a reference pixel value on the projection line of interest corresponds to a pixel of the first region of interest and the adjacent region of interest is the second region, and
a display unit for displaying the display image, wherein
the display image generator sets the reference pixel value on the projection line of interest as a projected pixel value for the projection line of interest, and determines a color value of a color attribute being different from that of the projected pixel value according to the size of the second region of interest, when the pixel having the reference pixel value on the projection line of interest corresponds to the pixel in the first region of interest, and
the display unit displays an image obtained by superimposing the color value on the display image, and wherein
the display image generator determines the color value, based on a number of pixels in the first region of interest being a region that is positioned on the projection line of interest and including the reference pixel value, and a number of pixels in the first region of interest being a region that is positioned on a projection line being adjacent to the projection line of interest and positioned on the periphery of the pixel having the reference pixel value.

4. The medical image display device according to claim 1, wherein,
the display image generator calculates a first index value indicating a ratio of pixels representing a tissue of interest in the adjacent region of interest, and determines a color value of a color attribute being different from that of the projected pixel value, according to the first index value, and
the display unit displays an image obtained by superimposing the color value on the display image.

5. The medical image display device according to claim 1, wherein
the display image generator calculates a first index value indicating a ratio of pixels representing a tissue of interest in the adjacent region of interest, further calculates a second index value indicating a ratio between a number of pixels in the first region of interest being a region that is positioned on the projection line of interest and including the pixel having the reference pixel value, and a number of pixels in the first region of interest being a region that is positioned on a projection line being adjacent to the projection line of interest and positioned on the periphery of the pixel having the reference pixel value, and determines a color value of a color attribute being different from that of the projected pixel value according to the first index value and the second index value, and
the display unit displays an image obtained by superimposing the color value on the display image.

6. The medical image display device according to claim 1, wherein,
when the reference pixel value corresponds to a maximum pixel value on the projection line of interest, the display image generator sets as the pixel value based on the group of pixels in the adjacent region of interest, an average pixel value of the adjacent region of interest or a minimum pixel value of the adjacent region of interest, and when the reference pixel value corresponds to a minimum pixel value on the projection line of interest, the display image generator sets as the pixel value based on the group of pixels in the adjacent region of interest, the average pixel value of the adjacent region of interest or a maximum pixel value of the adjacent region of interest.

7. A medical image display method comprising, a region of interest setting step of setting a first region of interest being a region of an observation site in volume data, and a second region of interest being a lesion candidate region relating to the observation site, a display image generating step of generating a display image that allows a size of an adjacent region of interest to be distinguishable, being the second region of interest adjacent to the first region of interest on a projection line of interest, when a pixel having a reference pixel value on the projection line of interest corresponds to a pixel of the first region of interest, and a displaying step of displaying the display image, wherein when the pixel having the reference pixel value on the projection line of interest corresponds to the pixel of the first region of interest, the display image generating step determines a weight coefficient according to the size of the adjacent region of interest, and sets a value as a projected pixel value for the projection line of interest, the value being weighted the weight coefficient to a pixel value based on a group of pixels in the adjacent region of interest and the reference pixel value on the projection line of interest.

\* \* \* \* \*